United States Patent [19]
Cartwright et al.

[11] Patent Number: 5,192,293
[45] Date of Patent: Mar. 9, 1993

[54] DRILL GUIDE FOR ORBITAL IMPLANT

[75] Inventors: Mont J. Cartwright, Laguna Niguel, Calif.; Christine C. Nelson, Ann Arbor, Mich.

[73] Assignee: The Regents Of The University Of Michigan, Ann Arbor, Mich.

[21] Appl. No.: 909,579

[22] Filed: Jul. 6, 1992

[51] Int. Cl.$^5$ .......................... A61B 17/32; A61F 2/14
[52] U.S. Cl. ...................................... 606/172; 606/80; 606/96; 606/167; 623/4
[58] Field of Search ............... 623/4; 606/79, 80, 166, 606/167, 172, 1

[56] References Cited

U.S. PATENT DOCUMENTS

| | | | |
|---|---|---|---|
| 2,401,548 | 6/1946 | Chapman | 606/172 |
| 2,649,590 | 8/1953 | Cutler | 623/4 |
| 2,810,134 | 10/1957 | Radin | 623/4 |
| 4,257,411 | 3/1981 | Cho | 606/96 |
| 4,821,716 | 4/1989 | Ghajar et al. | 606/172 |

*Primary Examiner*—Ronald Frinks
*Attorney, Agent, or Firm*—Harness, Dickey & Pierce

[57] ABSTRACT

This invention relates to a drill guide particularly useful for drilling an accurately located and oriented bore of limited depth into an orbital implant for purposes of fixating an orbital prosthesis. The drill guide comprises a cylindrical housing, the distal end of the housing defines a plurality of fixation pegs which are engagable with the orbital implant. An adaptor insert is placed on the nonrotating nose of a surgical drill which defines an outer diameter which is closely received by the drill guide housing. Features are provided to limit the depth of insertion of the adaptor insert. After placement of the drill guide on the orbital implant the surgical drill can be advanced until the physical stop is reached providing a limited depth bore which can be accurately located and oriented.

11 Claims, 1 Drawing Sheet

DRILL GUIDE FOR ORBITAL IMPLANT

BACKGROUND AND SUMMARY OF THE INVENTION

This invention relates to a surgeons tool for drilling a hole into an orbital implant for purposes of fixing an artificial eye.

When patients have an eye removed (enucleation or evisceration), an implant is placed into the socket to provide a base for extraocular muscle reattachment. In addition to cosmetic considerations, in younger patients an implant is also essential for appropriate socket growth. At a later date, a prosthesis painted to match the fellow eye is situated in the socket overriding the previously placed implant. It is important that the prosthetic movement match that of the fellow eye to minimize awareness by others that an artificial eye is present. Motility of the prosthesis is usually accomplished by reattaching the eye muscles to the buried implant that is placed first. This allows the socket tissues to move somewhat and the socket movement is partially translated to the prosthesis to move it as well.

Translation of motion between the socket and prosthesis is inefficient unless the system is integrated by some sort of connecting system between the prosthesis and the implant. Unfortunately, most of the early integrated implants were deemed unsatisfactory over the years because many of them became infected or extruded, necessitating removal. The hydroxyapatite implant is an integrated implant but because of its biocompatibility and biointegratability should have a lower rate of infection or extrusion than previous integrated implants. The hydroxyapatite implant is a microporous, corraline sphere which is covered by cadaver donor Eye Bank sclera to which the extraocular muscles are attached. The implant later becomes vascularized from the ingrowth of the host body tissues through its microporous structure. In several months when the implant is completely vascularized, it is drilled for placement of a peg that will later drive an overlying prosthesis.

Drilling the implant correctly can be difficult. It is imperative that the hole be properly positioned to maximize the even distribution of motility in all directions. The prosthesis will be contoured on its posterior aspect to accept the ball-shaped peg head, therefore, the peg must be so positioned to allow the prosthesis to be contoured in an area of sufficient bulk to accommodate the peg. The angulation of the hole is also important in that the peg should be presented perpendicular to the facial frontal plane. This also enhances motility and prevents peg slippage, since the ball is fitting perfectly into the posterior cavity of the prosthesis. Prior to this invention, the hole has been drilled free-handedly. There have been difficulties with maintaining orientation and depth of the drilling. When the drill touches the implant, it bobs within the socket as there is no fixation of the prosthesis to the socket tissue, except for the attached extraocular muscles. The drill may also slip off the hydroxyapatite implant during the drilling procedure and damage the surrounding socket tissue.

This invention is a drill guide that fixates the implant for drilling and also regulates the drilling depth. The drill guide incorporates contoured inserts which enable a variety of different drill designs to be employed. The drill guide is located over the implant and includes fixation features for supporting the implant during the drilling procedure. The device further allows consistent drilling to a predetermined depth and establishes a proper angular positioning of the drilled hole. The use of the device reduces conjunctival trauma, eliminates a need for a surgical assistant, and by encasing the drill, provides protection to the patient as compared with free-handed methods. Moreover, overall surgical time using the drill guide of this invention is decreased.

Additional benefits and advantages of the present invention will become apparent to those skilled in the art to which this invention relates from the subsequent description of the preferred embodiments and the appended claims, taken in conjunction with the accompanying drawings.

BRIEF DESCRIPTION OF THE DRAWINGS

FIGS. 3, 4 and 5 are cross-sectional views through a patient's eye socket showing, respectively, a drilled hole in the implant, insertion of a mounting peg, and completion of the procedure with mounting of the eye prosthesis.

DETAILED DESCRIPTION OF THE INVENTION

Figure 1:
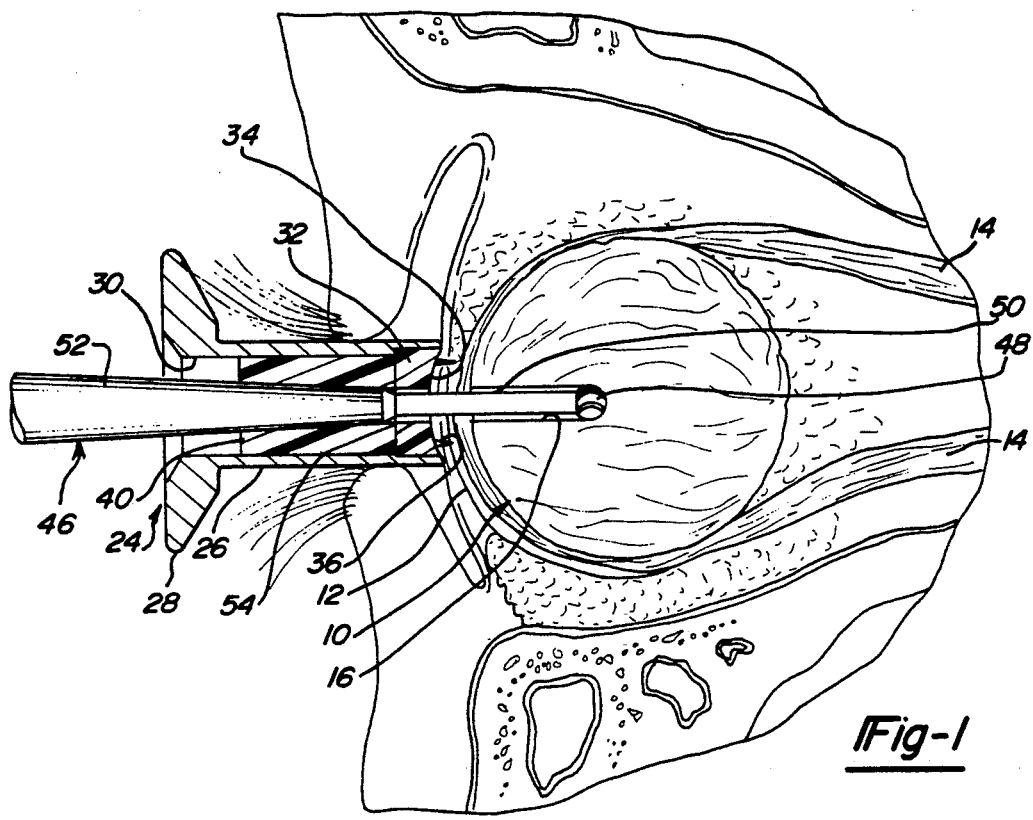
FIG. 1 is a cross-sectional view through a patient's eye socket area showing an implant in the process of being drilled using a drill guide in accordance with this invention.

With reference to FIG. 1 an implant made of hydroxyapatite material is shown implanted and integrated within a patient eye socket and is generally designated by reference number 10. Implant 10 is shown integrated within the patient's eye socket with conjunctiva tissue 12 covering the anterior surface of the implant. Implant 10 is shown in the process of having a drilled bore 16 formed with the aid of drill guide 24 of this invention. As shown in FIGS. 3, 4, and 5, bore 16 accommodates peg 18 which, after insertion, drives prosthesis 20 through a ball-and-socket joint. Since the placement of drill bore 16 determines the position of prosthesis 20, it is necessary to form the bore accurately. Moreover, bore 16 must have a precise depth to provide proper positioning of prosthesis 20.

Figure 2:
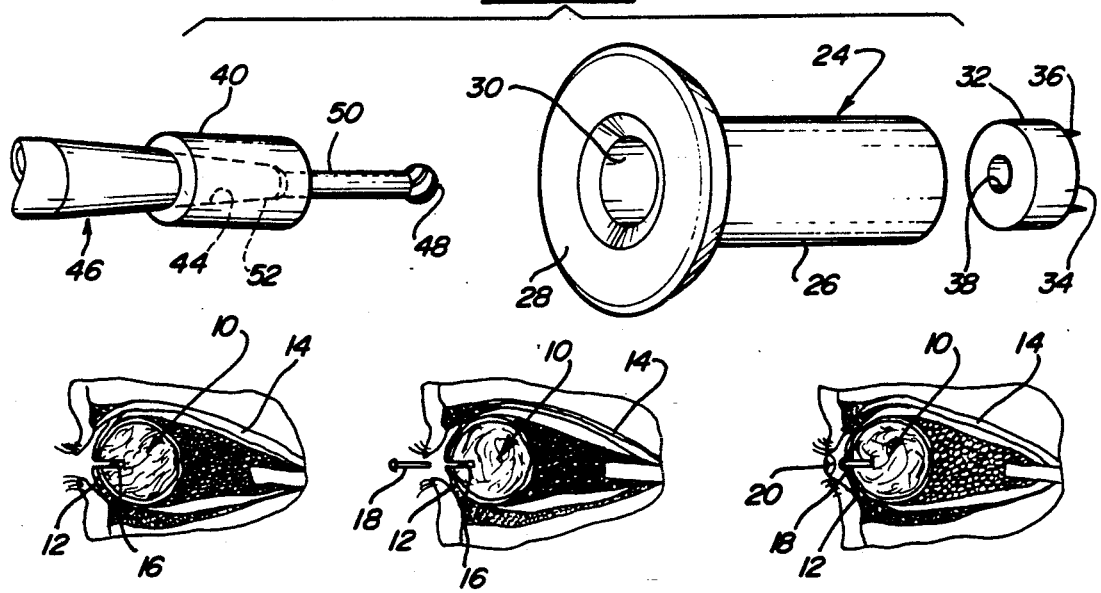
FIG. 2 is an exploded view of the drill guide in accordance with this invention shown with a surgical drill.

FIGS. 1 and 2 show features of drill guide 24 in accordance with this invention. Drill guide 24 includes a hollow cylindrical housing 26 having a flared rim 28 at its proximal end which is provided to facilitate handling by the surgeon. Housing 26 can be formed of various materials such as stainless steel. The interior bore 30 of the housing accommodates a pair of inserts. Fixed insert 32 is press-fit into the distal end of housing bore 30 and defines a concave end surface 34 shaped to generally conform to the radius of curvature of implant 10. A number of extending fixation pegs 36 having sharpened points are oriented around the perimeter of insert 32 and engage implant 10 during the drilling procedure. Insert 32 being press-fit into housing 26, remains in a fixed position during use, but can be removed to permit sterilization of housing 26. Bore 38 is centrally located through fixed insert 32 and is sufficiently large to provide clearance with drill burr 48.

Adapter insert 40 is provided which loosely fits within drill guide interior bore 30 thus allowing it to be freely slid into and out of the bore during the drilling operation, as will be explained in more detail below.

Inserts 32 and 40 can be made from various materials such as plastics suitable for surgical use.

FIGS. 1 and 2 show a typical surgical drill of the type used for drilling implant 10. The illustrated drill is a Ugo-Fisch model, although various other types could be used with this invention. Drill 46 is used with a rotary drill burr 48 at the end of tool shank 50. A tapered drill nose 52 surrounds the drill chuck (not shown) and does not rotate with the tool. Adaptor insert bore 44 is tapered to closely conform to drill nose 52 and acts as a means of aligning the drill relative to drill guide 24. Since the configuration of drill 46 shown in the Figures is only one of many of such devices available for implant drilling, various configurations of adapter inserts can be provided for use with specific drill types. Presently used drills, although differing somewhat dimensionally have the common characteristic of having a nonrotating nose such as that shown for drill 46. The various adaptor inserts would be dimensioned to closely conform to a particular drill nose. Each adapter insert would however have an outer cylindrical surface closely conforming with housing bore 30 which provides a small clearance enabling the insert to be slid into and out of the housing while maintaining alignment between the drill and the central axis of housing bore 30.

Prior to the process of drilling implant 10, the conjunctiva 12 at the proposed drilling site is infiltrated with local anesthesia and cauterized to expose implant 10. This step allows drill burr 48 to be in direct contact with the surface of implant 10 at the onset of drilling. A lid speculum (not shown) can be placed into the socket to provide access to the surgical area and the drill site is determined. The drill 46 with adaptor 40 attached is placed through drill guide 24 until the stop position is reached when inserts 32 and 40 contact one another and the distance which drill 48 extends from fixed insert 32 is measured to confirm the depth of the hole to be drilled. Adjustment in the depth of the hole can be provided by changing the depth that drill shank 50 is chucked within the drill. After the drilling depth is confirmed, drill guide 24 is centered over the conjunctival hole oriented perpendicular to the horizontal facial plane. With the patient in primary gaze, alignment between the prosthesis 20 and the fellow eye is maintained. Fixed insert bore 38 can be used as an aiming hole to properly position drill guide 24. Thereafter, posterior pressure is applied to drill guide 24 causing fixation pegs 36 to engage with conjunctival tissue 12 and the underlying implant 10, and drill 46 is again placed into the drill guide 24. Drill 46 is actuated and advanced until stopped. Thereafter, drill 46 is withdrawn and guide 24 can be removed and the hole irrigated. Peg 18 can thereafter be placed in position for supporting prosthesis 20.

In an alternate embodiment of this invention (not shown) the physical features of fixed insert 32 could be incorporated into an integral structure and thus the only separate component would be adapter insert 40. Through appropriate selection of materials, the device could also be made for single use applications.

While the above description constitutes the preferred embodiments of the present invention, it will be appreciated that the invention is susceptible of modification, variation and change without departing from the proper scope and fair meaning of the accompanying claims.

We claim:

1. A drill guide for use in drilling a hole in an orbital implant for placement of a prosthesis mounting peg using a surgical drill having a rotating drill burr and a nonrotating drill nose, comprising:
   a cylindrical housing assembly defining a proximal end and a distal end, said distal end defining a plurality of axially protruding fixation pegs, said housing assembly further having a central bore extending between said proximal and distal ends,
   an adaptor insert having an outer cylindrical surface dimensioned to freely slide into said housing bore and having an inside bore shaped to engage said drill nose, and
   stop means for allowing said adaptor insert to be displaced into said housing bore to a predetermined depth whereby when said distal end is placed against said implant and said adaptor insert is placed onto said drill nose, said drill is guided to form a hole in said implant of a limited depth.

2. A drill guide according to claim 1 wherein said housing further defines a radial flange adjacent said proximal end for aiding in manipulating said drill guide.

3. A drill guide according to claim 1 wherein said housing assembly comprises a hollow cylindrical tube having one or more inserts disposed therein defining said central bore.

4. A drill guide according to claim 3 wherein said housing assembly comprises a fixed insert disposed within said distal end of said housing and having a central bore having a diameter sufficient to provide clearance for said burr.

5. A drill guide according to claim 4 wherein said fixation pegs are mounted to said fixed insert.

6. A drill guide according to claim 4 wherein said fixed insert defines a concave end surface generally corresponding to a radius of curvature of said implant.

7. A drill guide according to claim 4 wherein said stop means comprises said adapter insert engagement with said fixed insert.

8. A drill guide for use in drilling a hole in an orbital implant for placement of a prosthesis mounting peg using a surgical drill having a rotating drill burr and a nonrotating drill nose, comprising:
   a cylindrical housing assembly defining a proximal end and a distal end, said housing assembly defining an internal bore
   a fixed insert disposed within said housing distal end defining a plurality of axially protruding fixation pins, and
   an adaptor insert having an outer cylindrical surface dimensioned to freely slide into said housing bore and having an inside bore shaped to engage said drill nose, whereby when said housing distal end is placed against said implant and said adaptor insert is placed onto said drill nose, said drill burr is guided to form a hole in said implant of a limited depth.

9. A drill guide according to claim 8 wherein said housing further defines a radial flange adjacent said proximal end for aiding in manipulating said drill guide.

10. A drill guide according to claim 9 wherein said fixed insert defines a central bore having a diameter sufficient to provide clearance for said burr.

11. A drill guide according to claim 8 wherein said fixed insert defines a concave end surface generally corresponding to a radius of curvature of said implant.

* * * * *